United States Patent
Friedberger et al.

(10) Patent No.: US 10,495,591 B2
(45) Date of Patent: Dec. 3, 2019

(54) SENSOR SKIN COMPRISING TEMPERATURE SENSORS

(71) Applicant: Airbus Defence and Space GmbH, Taufkirchen (DE)

(72) Inventors: Alois Friedberger, Oberpframmern (DE); Andreas Helwig, Munich (DE)

(73) Assignee: AIRBUS DEFENCE AND SPACE GMBH, Taufkirchen (DE)

( * ) Notice: Subject to any disclaimer, the term of this patent is extended or adjusted under 35 U.S.C. 154(b) by 219 days.

(21) Appl. No.: 15/619,971

(22) Filed: Jun. 12, 2017

(65) Prior Publication Data
US 2017/0356866 A1 Dec. 14, 2017

(30) Foreign Application Priority Data

Jun. 13, 2016 (EP) .................................... 16174251

(51) Int. Cl.
| | |
|---|---|
| *G01K 17/00* | (2006.01) |
| *G01K 7/00* | (2006.01) |
| *G01N 25/72* | (2006.01) |
| *B64F 5/60* | (2017.01) |
| *B64C 1/00* | (2006.01) |

(52) U.S. Cl.
CPC ............... *G01N 25/72* (2013.01); *B64F 5/60* (2017.01); *B64C 2001/0072* (2013.01)

(58) Field of Classification Search
USPC .......................................... 374/4, 5, 57, 166
See application file for complete search history.

(56) References Cited

U.S. PATENT DOCUMENTS

| | | | |
|---|---|---|---|
| 5,726,744 A | 3/1998 | Ferdinand et al. | |
| 5,772,329 A * | 6/1998 | Bardon ................... | G01K 17/20 374/166 |
| 6,137,669 A * | 10/2000 | Chiang ..................... | G01K 3/14 361/103 |
| 6,462,329 B1 | 10/2002 | Davis et al. | |

(Continued)

FOREIGN PATENT DOCUMENTS

| | | |
|---|---|---|
| EP | 0713084 | 5/1996 |
| WO | 0120380 | 3/2001 |

(Continued)

OTHER PUBLICATIONS

European Search Report.
International Search Report, May 19, 2008 priority document.

*Primary Examiner* — Mirellys Jagan
(74) *Attorney, Agent, or Firm* — Greer, Burns & Crain, Ltd.

(57) ABSTRACT

A measurement arrangement for detecting damage to components that are made of at least one fiber-reinforced plastic material, has a plurality of temperature sensors that are arrangeable or arranged on a component at a spacing from one another. In order to provide a measurement arrangement, by means of which temperature data can be cost-effectively obtained during the production and operation of a component and for it to thus be possible for damage to the component to be recorded and monitored, the plurality of temperature sensors on the component form a sensor array and a change in the thermal material properties of the component is detected by means of the sensor array.

19 Claims, 2 Drawing Sheets

(56) References Cited

U.S. PATENT DOCUMENTS

| | | | |
|---|---|---|---|
| 7,699,520 B2 * | 4/2010 | Yoo | G01K 17/20 |
| | | | 374/29 |
| 2001/0028763 A1 | 10/2001 | Carberry et al. | |
| 2006/0133190 A1 * | 6/2006 | Manz | B01F 3/188 |
| | | | 366/107 |
| 2010/0080501 A1 | 4/2010 | Saunders et al. | |
| 2011/0034912 A1 * | 2/2011 | de Graff | H01L 27/14687 |
| | | | 606/21 |
| 2012/0263209 A1 * | 10/2012 | Panda | G01K 1/143 |
| | | | 374/163 |
| 2013/0333094 A1 * | 12/2013 | Rogers | A61B 5/01 |
| | | | 2/161.7 |

FOREIGN PATENT DOCUMENTS

| | | |
|---|---|---|
| WO | 0138838 | 5/2001 |
| WO | 03076887 | 9/2003 |
| WO | 2008090348 A1 | 7/2008 |

\* cited by examiner

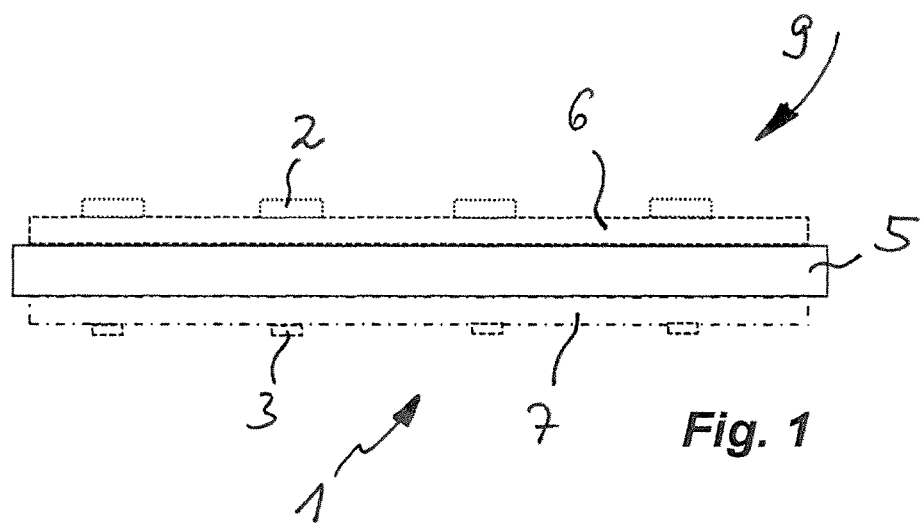
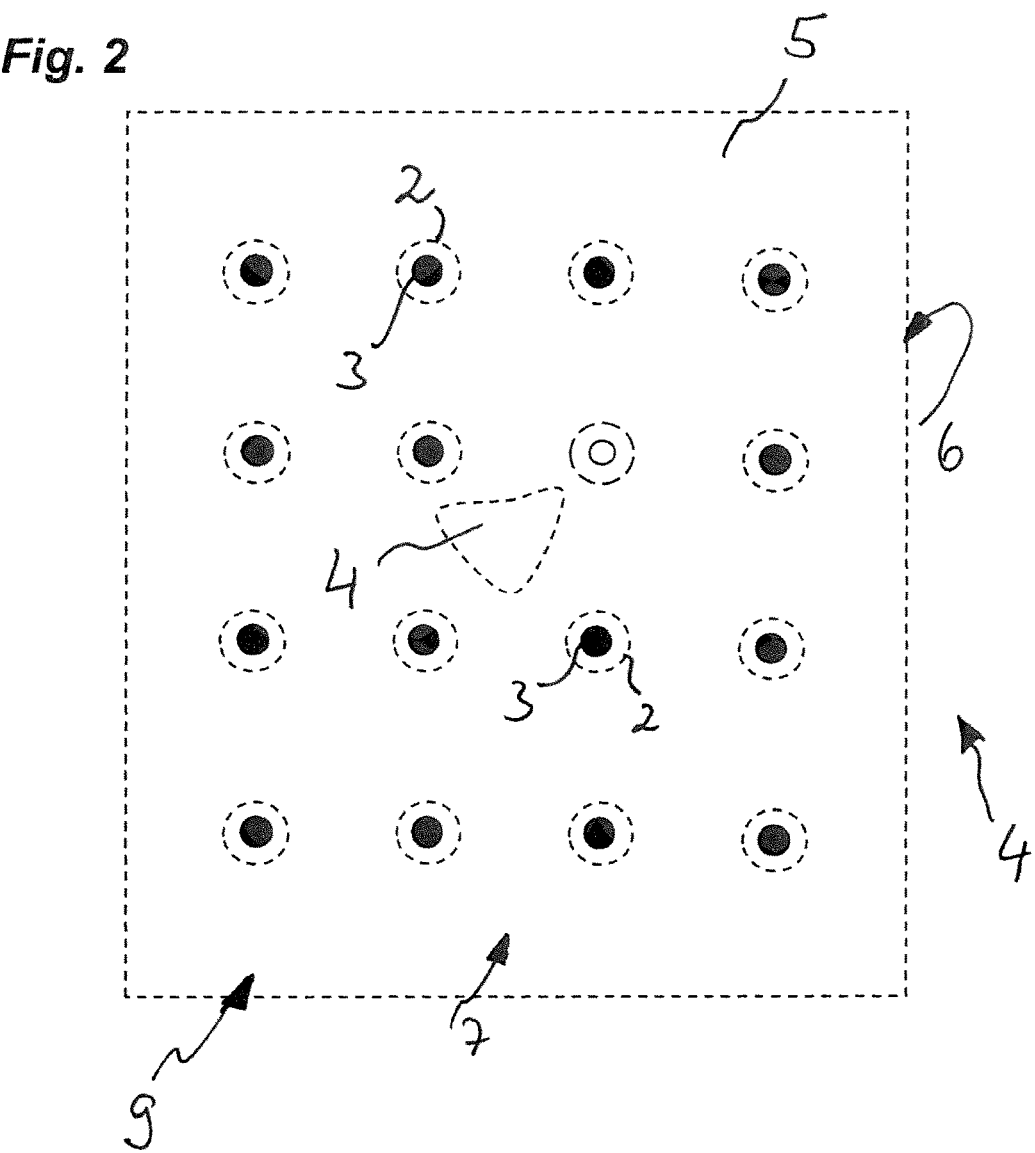

SENSOR SKIN COMPRISING TEMPERATURE SENSORS

CROSS-REFERENCES TO RELATED APPLICATIONS

This application claims the benefit of the European patent application No. 16174251.5 filed on Jun. 13, 2016, the entire disclosures of which are incorporated herein by way of reference.

FIELD OF THE INVENTION

The invention relates to a measurement arrangement for detecting damage to components that are made of at least one fiber-reinforced plastic material, comprising a plurality of temperature sensors that are arrangeable or arranged on a component at a spacing from one another. The component can be a constituent of an aircraft or spacecraft, for example.

BACKGROUND OF THE INVENTION

In aircraft construction, whenever developing lighter and safer aircraft, monitoring the structural integrity (SHM) is also always an essential field, the substantial aim of which is to monitor and observe damage to structures. Detecting damage and measuring the severity thereof are critical features for subsequent decision-making. In this case, the development of structures based on materials other than metals requires modified monitoring and damage-detection methods.

Since more and more aircraft or spacecraft parts were being made of fiber-reinforced plastic materials, approaches for assessing damage to such structures had to be developed, these including, inter alia, ultrasonic measurement methods, thermography, electrical potential measurements and vibration-based tests.

Due to the dimensions of aircraft and spacecraft in particular, the costs associated with the known methods are substantial and these methods are generally only suitable for monitoring during maintenance intervals, and not during operation of the aircraft or spacecraft.

Another method proposes analyzing the thermal behavior of fiber-reinforced plastic materials (CFRPs), which appears to be promising, since it is possible to record how external influences can act on the quality of heat dissipation in the material, for example, in a more cost-effective manner, and this can be used to make statements relating to damage. However, introducing thermal sensors into the matrix of the plastic material of the component in question during maintenance/inspection renders the component unusable in principle, and data from the operation of the component cannot be obtained by the sensors. Lastly, it would be desirable to be able to make statements relating to the production process of the plastic component without having to provide an additional costly test setup for this.

SUMMARY OF THE INVENTION

One of the ideas of the present invention is therefore to provide a measurement arrangement, by means of which temperature data can be cost-effectively obtained during the production and operation of a component, and damage to the component can thus be recorded and monitored.

The invention accordingly comprises, in particular, in forming at least one sensor array with the temperature sensors or temperature transducers on the component, and in using the at least one sensor array to detect a change in the thermal material properties. The invention therefore, in particular, comprises the possibility of using the plurality of temperature sensors not just to measure the temperature at selected points on the component, but, in fact, to detect delaminations and damage to the structure by means of a change in the thermal properties of the material, and specifically, as will be shown hereinafter, in particular, a change in the thermal conductivity thereof or the temperature distribution in the component. This takes advantage, inter alia, of the effective heat conductivity of fiber-reinforced plastic materials (CFRPs). A plurality of sensor arrays can also be provided for this purpose.

In an embodiment of the measurement arrangement according to the invention, which provides a multiplicity of different possible arrangements of the plurality of temperature sensors in a sensor array on the component, a plurality of temperature sensors is arranged on a flexible substrate, for example a suitable film, and is already integrated in the component during the production stage. This effectively provides the component with the additional ability of monitoring, essentially by itself, both temperature values and process parameters during the production of the component and the influence of potentially damaging events on the structural integrity thereof during operation, in a cost-effective and reliable manner and with a reasonable amount of effort, so that the corresponding data is in principle available at all times. In this case, the flexible substrate provided with the temperature sensors forms a kind of sensor skin.

In another embodiment, on the one hand, the sensor skin comprising the flexible substrate can be arranged on the component surface, and, on the other hand, it can also have been integrated inside the matrix during a joining process of the component in question, in which two structural elements are bonded, and therefore it is also possible to obtain values from inside the component by means of the sensors.

In a robust embodiment of the measurement arrangement, the flexible substrate itself can also expediently be bonded to the matrix of the component when producing the component.

In order to also be able to obtain values regarding a temperature distribution on non-planar structures of the component, either in its interior or on its surface, and to also be able to measure spatially more complex structures, in another embodiment of the measurement arrangement, according to the invention, the flexible substrate can occupy or cover a curved surface of the component when in use.

In order to obtain a kind of spatial resolution using the temperature sensors arranged on the flexible substrate when detecting damage, an additional embodiment of the measurement arrangement can provide distributing, in particular equally in this case, the plurality of sensors over the flexible substrate. In this case, the sensors can form a kind of grid with adjacent sensors meshing, which grid, to some extent, also allows for an extension in a direction that is perpendicular to the planar extension of the flexible substrate.

In order to be able to assess the development of temperature distributions, and therefore of damage, which may not have been noticed yet, to a component structure at any time, an expedient development of the measurement arrangement comprising a heating device having at least one heating element can be provided, so that heat can be introduced into the structure at all times. In various scenarios, which can be made dependent on the desired degree of detection accuracy, for example, at least one heating element can be expediently assigned to each group of sensors or one heating element can be expediently assigned to each sensor. However, each sensor can also comprise its own heating element and/or the number of heating elements of the heating device can be independent of the number of heating elements of the sensors.

In expedient developments of the measurement arrangement, separate heating elements can be arranged on the same flexible substrate as the temperature sensors, or the heating elements and the temperature sensors can be arranged on different flexible substrates that are connected to the component when it is produced. It is conceivable, for example, to arrange the temperature sensors and the heating elements on separate substrates in each case, and in turn to connect the substrates to two surfaces, which face away from one another, of a component that may be very thin. In this way, it is possible to provide each of these surfaces per se with a sensor skin; in this regard "sensor skin" must be understood in a broader context since, as explained below, it is in principle also possible to use sensors for heating.

Another embodiment of the measurement arrangement, which allows for a flexible arrangement of the heating device and sensors, can provide arranging the heating device, comprising the at least one heating element, and the plurality of sensors, in particular the sensor array, on the same side or surface of the component or on different sides or surfaces.

In order to be able to directly evaluate the temperature data obtained by means of the measurement arrangement, in another development, the measurement arrangement according to the invention can be provided with at least one control and evaluation device. This can, in particular, be used to plan and initiate heating events and to control the heating elements and the temperature sensors. In this case, selectively determined regions provided with sensors and/or heating elements or individual sensors/elements on the component, for example, can also be actuated in isolation. For example, if sensors were to fail due to previous structural damage (for example by an impact event), sensors that are still working properly can also take over the work of failed sensors, this distribution/control can also be taken over by the control and evaluation device. At least one storage means can also be assigned to the control and evaluation device, by means of which storage means control parameters, measurement results and/or evaluation results can be stored and kept available for further processing, for example.

In a development of the measurement arrangement according to the invention, such a control and evaluation device can, for example, be integrated in the particular flexible substrate.

The detection of damage to the component structure is detected by the sensor array on the sensor skin. A change in the ambient temperature or the introduction of temperature loads first very generally leads to a distribution of the temperature load according to the thermal properties of the component. Damage to the component, for example caused by an impact event (already mentioned), leads to a change in the ability to pass on the temperature loads or to distribute them over the structure of the component. In another embodiment, it is therefore provided that the measurement arrangement according to the invention records and optionally evaluates a time-dependent temperature distribution and/or a maximum distribution of the temperature and (/or) a duration of the temperature when a temperature load is introduced into the component. The magnitude of the damage is reflected in the intensity of the measured variable, while the spatial resolution is carried out via the sensor array. The sensor density of the arrangement is essentially determined by the magnitude of the damage that is considered to be relevant.

In a development, various measurement methods, in particular at least one active and/or one passive measurement method, can expediently be carried out using the measurement arrangement according to the invention. These can optionally be carried out completely independently of one another at the same time in one measuring situation using different numbers of sensors, or one after the other still in the same measurement situation, or even in different measurement situations. Other feasible measurement methods are also conceivable.

An active measurement method, which the measurement arrangement according to the invention carries out, can, for example, comprise such that, during flight operation or in any other operation, thermal loading is introduced into the component structure by means of heating elements, the component is thus exposed to thermal loading at any time and the development of the temperature distribution is then observed, for example.

In another variant, the measurement arrangement according to the invention can carry out a passive measurement method, for example, in that the temperature differences between the earth's surface (for example 20° C. on an airfield) and the operational altitude (for example up to minus 80° C. at an operational altitude of up to 20 km), can be used to generate a temperature gradient. In this case, the gradient is really noticeable during the ascent and the descent, the temperature sensors tracking the gradient and, if differences occur, the comparison of signals from individual sensors, in particular, allows for first assessments regarding the presence of any damage.

In order to be able to integrate heating elements in the flexible substrate, in a development of the measurement arrangement the heating elements can, for example, be formed as micromechanical systems, what are known as microheaters. However, other designs are also possible. Furthermore, the temperature sensors can each also be used as heating elements, for example provided they have corresponding correct dimensions.

A reliable arrangement on the particular component is achieved using a flexible substrate, in which the thermoplastic high-performance plastic material is made of a polyimide, in particular polyetherimide, or a polysulfone, in particular polyethersulfone. Each of these materials form suitable film materials which, during the particular production process, reliably bind to the plastic matrix of the component and form a type of sensor skin thereon.

Metal conducting tracks for heating elements and temperature sensors can also interrupt the component matrix. In order not to adversely affect the mechanical properties of the composite structure as a result, a development of the measurement arrangement can comprise forming at least one or a plurality of or all the heating elements of the heating device and/or to form at least one or a plurality of or all the temperature sensors as a conductive polymer in each case. This can be integrated in the flexible substrate in each case or can even form the substrate itself.

Another embodiment can comprise doping the flexible substrate and/or another carrier foil to different extents or in processing the flexible substrate in some other way, for example. For this purpose, a conductive film can be used, for example, and the conductivity thereof can be interrupted at corresponding points in order to generate the desired conducting tracks as a result.

In one use of the measurement arrangement, the heating elements of the heating device can also be used, irrespective of their design, for anti-icing, in order to help prevent components from icing over or to counteract or remedy this, for example on an airfoil, due to weather influences, for example, or as a result of the operational height of the aircraft.

The above embodiments and developments can be combined in any way, within reason. In particular, it is, for example, also conceivable to achieve improved spatial resolution by arranging a plurality of sensor skins. Furthermore, additional sensors that record other parameters, for example pressure sensors or sensors that capacitively record the degree of crosslinking of the polymer of the component, can also be provided. These not only provide redundancy, but may also increase the reliability of assessing damage particularly well. Further possible embodiments, developments and implementations of the invention also include combinations (not explicitly mentioned) of features of the invention which are either described above or in the following in relation to the embodiments. In particular, a person skilled in the art will also add individual aspects to each basic form of the present invention as improvements or additions.

BRIEF DESCRIPTION OF THE DRAWINGS

The invention will be explained in greater detail in the following on the basis of embodiments shown in the partially schematic drawings, in which FIG. 1 is a sectional, planar lateral view of a first embodiment of the measurement arrangement, comprising two substrates that are arranged on opposite sides of a flat component and are provided with sensors or heating elements;

FIG. 2 is a planar lateral view of a component comprising a measurement arrangement from FIG. 1, in which the component has been damaged, it being intended for the damage to be detected by one of the heating elements heating up.

In all the drawings, like or functionally like elements and apparatuses have been provided with the same reference numerals, unless specified otherwise.

DETAILED DESCRIPTION OF THE PREFERRED EMBODIMENTS

Figure 3:
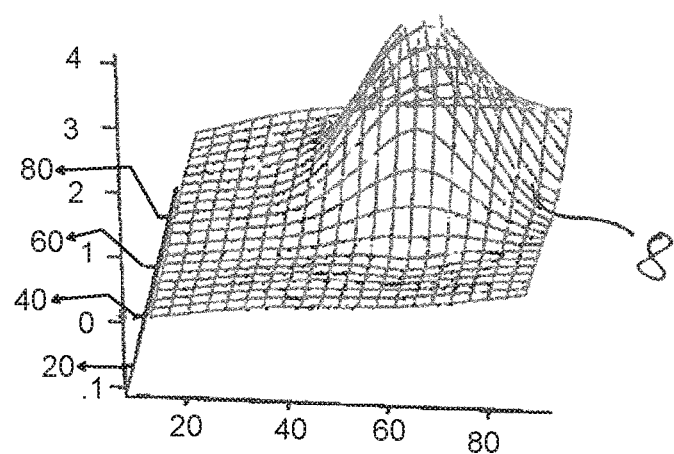
FIG. 3 is a graph of a temperature distribution shown in FIG. 2 resulting from the damage to the component.

FIGS. 1 and 2 show a measurement arrangement, designated as a whole by reference numeral 1, for detecting damage to components 5 that are made of at least one fiber-reinforced plastic material, comprising a plurality of temperature sensors 2 and temperature transducers that are arranged on the relevant portion (planar in this case) of a component 5 at a spacing from one another.

In the sectional view in FIG. 1, a component 5 is shown in the center, on each of the flat sides of which a flexible substrate 6, 7 is arranged. Temperature sensors are attached to the film-like substrate 6, which is arranged on the flat side of the component 5 that is at the top for the viewer, and are connected to the component 5 by the substrate. The same applies to the flexible substrate 7 arranged on the underside, by means of which heating elements 3 are connected to the component. Both substrates 6, 7 are bonded to the matrix of the component 5 when producing the component. In the component 5 in FIG. 1, each temperature sensor 2 of one of the substrates 6 is assigned a heating element 3 of the other substrate 7, without this having to influence the evaluation.

For this purpose, the measurement arrangement 1 known from FIG. 1 is shown in a planar view, in which the flat side comprising the heating elements 3 arranged on the substrate 7 is facing the viewer. If the 16 sensors 2 and heating elements 3 shown are enumerated, starting from the top-left position and starting with a row followed by a column, it will be seen that the heating element in position 2/3 is heated in order to apply thermal loading to the structure of the component 5, as a result of which the delamination 4 can be detected as damage. For the detection, all 16 temperature sensors shown in positions 1/1 to 4/4 can be used in this case. A temperature distribution over the flexible substrate 6 can be recorded and evaluated by the sensors 2 (as well as the heating elements 3) that form a grid 9 on the substrate thereof.

The graph in FIG. 3 shows the result of such an evaluation, in which a temperature distribution 8 is shown which, in the damage in FIG. 2, results from the evaluation by all the sensors 2 shown there. In the three-dimensional graph of the temperature distribution 8, by way of example a maximum temperature deviation from a target or reference value is plotted over the spatial, two-dimensional extension of the sensor array 9 in principally arbitrary units, as a result of which the detection of the delamination 4 in FIG. 2 can be seen clearly.

The above-described invention accordingly thus relates to a measurement arrangement 1 for detecting damage to components 5 that are made of at least one fiber-reinforced plastic material, comprising a plurality of temperature sensors 2 that are arrangeable or arranged on a component 5 at a spacing from one another.

In order to provide a measurement arrangement 1, by means of which temperature data can be cost-effectively obtained during the production and operation of a component 5 and damage to the component 5 can thus be recorded and monitored, the temperature sensors 2 are arranged on at least one flexible substrate 6 and the flexible substrate 6 is bonded to the matrix of the component 6 when producing the component.

As a result, a measurement arrangement 1 is established, by means of which it is possible to monitor the production of CFRP components 5 as well as to monitor the components and detect damage during operation, such that separate systems can be dispensed with in this connection. For this purpose, a film is provided as a flexible substrate 6 having a very high density of sensors 2 or transducers and integrated electronics functionality, which film is integrated in the component 5 to be monitored. As a result, a single system is provided for process monitoring and detecting damage, which, owing to the integrated electronics system, does not require any wiring and allows for simple signal evaluation and damage localization by active and passive temperature measurement, this in principle being able to take place at any time, i.e., also in flight.

Although the present invention has been described above by way of embodiments, it is not limited thereto, but can be modified in various ways. In particular, the invention can be varied or modified in multiple ways, without departing from the basic concept of the invention.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A measurement arrangement for detecting damage to components that are made of at least one fiber-reinforced plastic material, comprising
 a plurality of temperature sensors, arranged or arrangeable on a component at a spacing from one another,
 wherein the plurality of temperature sensors on the component form at least one sensor array,
 wherein a change in the thermal material properties of the component can be detected by the at least one sensor array, and
 wherein the measurement arrangement is provided with a control and evaluation device.

2. The measurement arrangement of claim 1, wherein the plurality of temperature sensors are arranged on at least one flexible substrate.

3. The measurement arrangement of claim 1, wherein a flexible substrate is arranged inside the component or on the surface thereof.

4. The measurement arrangement of claim 1, wherein a flexible substrate is bonded to a matrix of the component when producing said component.

5. The measurement arrangement of claim 1, wherein, when in use, a flexible substrate one of occupies or covers a curved surface of the component.

6. The measurement arrangement of claim 1, wherein the plurality of sensors are distributed evenly over a flexible substrate.

7. The measurement arrangement of claim 1, wherein the control and evaluation device of the measurement arrangement is integrated in a flexible substrate.

8. The measurement arrangement of claim 1, wherein the measurement arrangement records and optionally evaluates one of
 a time-dependent temperature distribution,
 a maximum distribution of the temperature, or
 a duration of the temperature when a temperature load is introduced into the component.

9. The measurement arrangement of claim 1, wherein various measurement methods, comprising at least one of at least one active or one passive measurement method, can be carried out using the measurement arrangement.

10. The measurement arrangement of claim 1, wherein the temperature sensors are each usable or used as heating elements.

11. The measurement arrangement of claim 1, wherein the thermoplastic high-performance plastic material is made of one of a polyetherimide, or a polyethersulfone.

12. The measurement arrangement of claim 1, wherein at least one of:
 at least one of the sensors,
 a plurality of the sensors,
 all of the sensors,
 at least one of a plurality of heating elements,
 a plurality of the heating elements, or
 all of the heating elements,
 are each formed as a conductive polymer.

13. The measurement arrangement of claim 1, wherein at least one of
 a particular flexible substrate on which the sensors are arranged, or
 a different carrier film on which the sensors are arranged, are either doped to different extents or processed in some other way.

14. The measurement arrangement of claim 1, wherein the measurement arrangement is provided with a heating device comprising at least one of:
 at least one heating element,
 at least one heating element being assigned to a group of the sensors,
 one heating element being assigned to each sensor,
 each sensor having its own heating element, or
 the number of heating elements of the heating device being independent of the number of heating elements of the sensors.

15. The measurement arrangement of claim 14, wherein one of:
 the at least one heating element of the heating device is arranged on the same flexible substrate as the temperature sensors, or
 the at least one heating element and the temperature sensors are arranged on different flexible substrates that are connected to the component when it is produced.

16. The measurement arrangement of claim 14, wherein the heating device, which comprises the at least one heating element, and the plurality of sensors comprising the sensor array, are arranged on one of the same side or surface of the component or on different sides or surfaces.

17. The measurement arrangement of claim 14, wherein the heating elements of the heating device are formed as microheaters.

18. A method for detecting damage to components that are made of at least one fiber-reinforced plastic material, with a measurement arrangement, comprising
 a plurality of temperature sensors, which are arranged or arrangeable on a component at a spacing from one another,
 wherein the plurality of temperature sensors on the component form at least one sensor array, and
 wherein the measurement arrangement is provided with a heating device having at least one heating element, and
 the method comprising the steps of
  applying heat to the component with the at least one heating element,
  measuring the temperatures of the component with the plurality of temperature sensors, and
  detecting a change in the thermal material properties of the component based on the temperatures sensed by the plurality of temperature sensors.

19. A measurement arrangement for detecting damage to components that are made of at least one fiber-reinforced plastic material, comprising
 a plurality of temperature sensors, arranged or arrangeable on a component at a spacing from one another,
 wherein the plurality of temperature sensors on the component form at least one sensor array,
 wherein a change in the thermal material properties of the component can be detected by the at least one sensor array, and
 wherein various measurement methods, comprising at least one of at least one active or one passive measurement method, can be carried out using the measurement arrangement.

* * * * *